United States Patent [19]

Jensen et al.

[11] Patent Number: 5,134,875
[45] Date of Patent: Aug. 4, 1992

[54] BREATH ALCOHOL SIMULATOR SOLUTION CONTAINERS AND METHOD OF USING SAME

[76] Inventors: Richard E. Jensen, Rte. 1, Box 190A, St. Peter, Minn. 56082; Donald H. Nichols, 225 Acorn Rd., Roseville, Minn. 55113

[21] Appl. No.: 589,988

[22] Filed: Sep. 28, 1990

[51] Int. Cl.$^5$ ............................................. G01D 18/00
[52] U.S. Cl. ........................................ 73/1 G; 436/9; 383/5; 383/37; 383/104
[58] Field of Search ................ 73/1 G; 436/9; 383/5, 383/37, 104

[56] References Cited

U.S. PATENT DOCUMENTS

| | | | |
|---|---|---|---|
| D. 291,355 | 8/1987 | Stanuch et al. | D24/17 |
| 3,380,646 | 4/1968 | Doyen et al. | 383/104 |
| 3,437,258 | 4/1969 | Kugler | 383/104 |
| 3,715,074 | 2/1973 | Michel | 383/122 |
| 3,842,345 | 10/1974 | Padgitt et al. | 324/71.1 |
| 3,847,551 | 11/1974 | Hutson | 436/9 |
| 3,854,319 | 12/1974 | Burroughs et al. | 73/1 G |
| 3,885,414 | 5/1975 | Reville | 73/1 G |
| 3,935,993 | 2/1976 | Doyen et al. | 383/104 X |
| 3,948,604 | 4/1976 | Hoppesch | 73/1 G X |
| 3,980,225 | 9/1976 | Kan | 383/104 |
| 4,353,497 | 10/1982 | Bustin | 383/104 |
| 4,391,777 | 7/1983 | Hutson | 422/84 |
| 4,407,152 | 10/1983 | Guth | 73/1 G |
| 4,495,418 | 1/1985 | Hutson | 250/343 |
| 4,708,938 | 11/1987 | Hickinbotham | 222/95 X |
| 4,837,849 | 1/1989 | Erickson et al. | 383/104 |

*Primary Examiner*—Tom Noland
*Attorney, Agent, or Firm*—Moore & Hansen

[57] ABSTRACT

A container for breath alcohol simulator solution comprising a self-standing 4 mil polyethylene bag having a removable label designating the quantity and calibration concentration of the fluid contained within the bag. The label may be removed from the bag and affixed to the breath alcohol simulator. A plurality of the filled bags are packaged in an upstanding position within a front and top opening carton having a pivoting lid for transportation, storage and use. The bag may be torn open and the fluid contents poured into a cavity within the breath alcohol simulator, or the bag may be opened and placed partially or entirely within the breath alcohol simulator with a gas inlet extending into the bag beneath the fluid level. Alternatively, the bag may be placed within a breath alcohol simulator having a gas inlet or outlet equipped to puncture the bag, with the simulator solution then being discharged into the cavity, or the air passed through the simulator solution within the bag. In such a case, a mechanism for agitating the simulator solution within the bag may be placed within the bag prior to sealing, or may be disposed on the portion of the gas inlet or outlet which punctures and enters the bag.

16 Claims, 2 Drawing Sheets

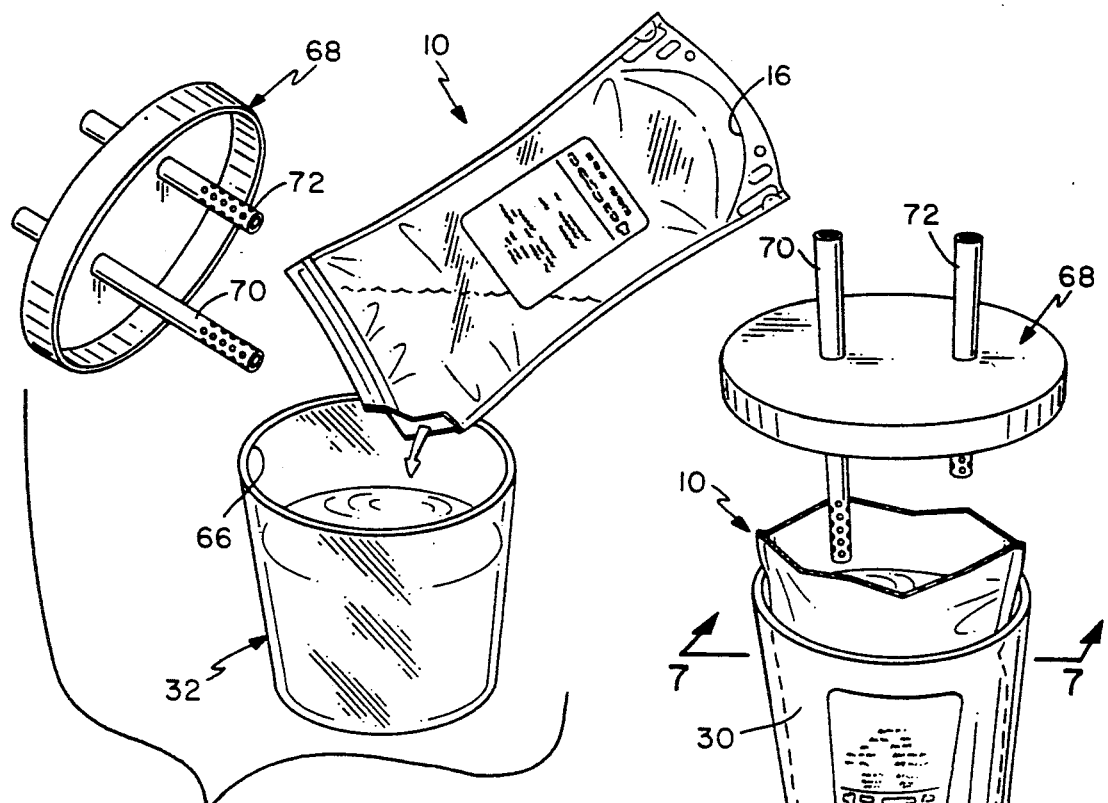
FIG. 5
FIG. 6
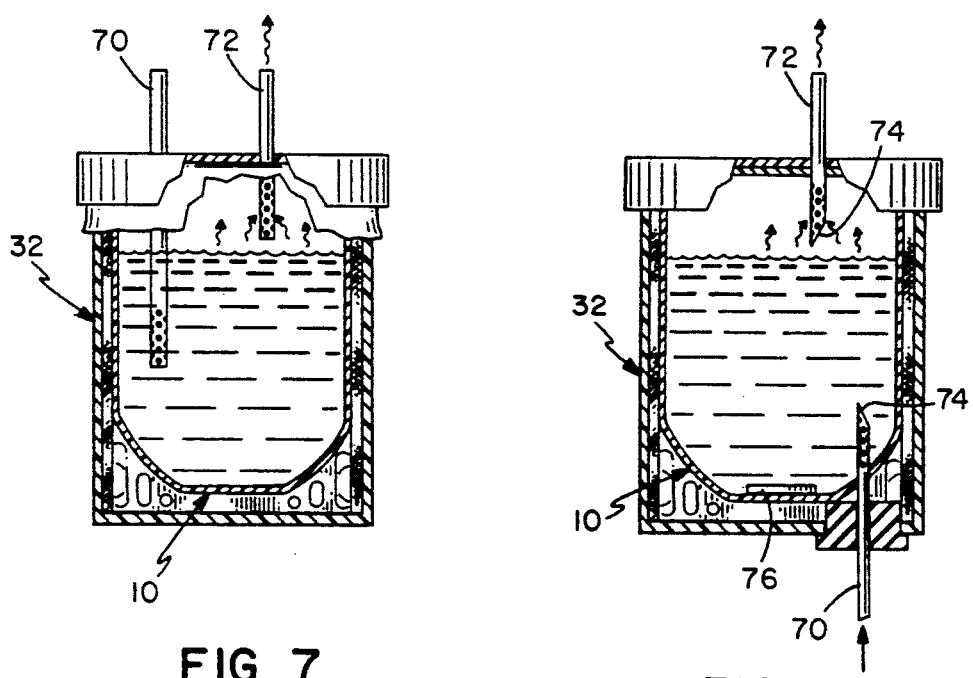
FIG. 7
FIG. 8

BREATH ALCOHOL SIMULATOR SOLUTION CONTAINERS AND METHOD OF USING SAME

BACKGROUND OF THE INVENTION

This invention relates generally to a container for a fluid breath alcohol simulator solution used to calibrate breath alcohol testing equipment, and a method for using such a container with breath alcohol simulators.

Several methods exist for directly or indirectly testing blood alcohol concentrations in individuals. Among the indirect methods, the most frequently used is breath alcohol testing Breath alcohol testing involves measuring the alcohol vapor level or concentration in a contained sample of expelled breath, that concentration being proportionally related to the individual's blood alcohol level.

Breath alcohol testers (commonly referred to as Breathalyzers TM) generally function using one of two conventional methods: fuel cells or infra-red absorption.

Breath is expelled under pressure through a tube having a gas pressure sensor into a chamber having a predetermined volume. The temperature of the gas may also be measured, or a standard body temperature constant may be utilized. The pressure sensor is coupled to a control circuit which calculates when the volume of air having entered the chamber reaches the predetermined volume, and either closes a control valve in response to a predetermined volume of air being admitted or signals the operator to cease expelling air.

In a fuel cell type breath alcohol tester, the predetermined volume of air contained within the chamber is passed between two platinum electrodes The alcohol vapor in the air produces a chemical reaction with the platinum electrodes, the extent or rate of the reaction being proportional to the concentration of alcohol molecules in the air contacting the platinum electrodes. The chemical reaction stimulates an electric voltage in or between the electrodes which is proportional to the concentration of alcohol molecules incident with the electrodes. A microprocessor measures the voltage and translates that value to either a breath alcohol concentration or an estimated blood alcohol concentration.

In an infra-red absorption type breath alcohol tester, one or more infra-red light beams are directed through the predetermined volume of air. A spectrometer or infra-red sensors measure the percentage of infra-red radiation at a discrete frequency which is transmitted through the air. The frequency of the infra-red radiation measured corresponds to the frequency which is absorbed by ethanol molecules The percentage of absorbed infra-red radiation (or the reciprocal of the transmitted radiation) is proportional to the concentration of alcohol molecules within the air, and a microprocessor determines the value of the absorbed infra-red radiation and translates that value to either a breath alcohol concentration or an estimated blood alcohol concentration The chamber of the breath alcohol tester is then purged, and a new sample may be collected.

In practice, both fuel cell or infra-red absorption breath alcohol testers must be calibrated periodically. Statutes and regulations proscribing the use of breath alcohol testers in criminal investigations or substance abuse testing vary between jurisdictions, however recalibration as frequently as every twenty tests is a common rule, and recalibration as a part of each test may be called for in some circumstances.

In order to calibrate the breath alcohol testers, it is necessary to introduce a gas having a known alcohol vapor concentration into the chamber of the breath alcohol tester under normal operating conditions. This is accomplished using a device known as a breath alcohol simulator.

In principle, the breath alcohol simulator functions by passing or bubbling air (or an inert gas) through a simulator solution or liquid having a fixed fluid concentration of alcohol and a controlled temperature. The air or gas absorbs a specific molar amount of alcohol molecules, and is therefore expelled from the breath alcohol simulator having a known alcohol-to-air concentration. For example, a simulator solution may be prepared so that when it is utilized in a particular type of breath alcohol simulator, the air expelled by the breath alcohol simulator will have an alcohol concentration equivalent to a specific reading (breath alcohol or estimated blood alcohol) to be displayed by the breath tester, most frequently a critical value for legal intoxication.

Through laboratory analysis and certification of samples of the simulator solution, operators of breath testers and breath simulators can be assured that the equipment is providing uniform and accurate measurements when used.

Representative examples of various types of this and other types of breath alcohol simulators are shown in U.S. Pat. Nos. 4,407,152 to Guth; 3,948,604 to Hoppesch; 3,854,319 to Burroughs; 4,495,418 to Hutson; 4,391,777 to Hutson; 3,847,551 to Hutson; 3,842,345 to Padgitt; and D291,355 to Stanuch.

The simulator solutions provided for use in the breath alcohol simulators are currently packaged and provided in containers such as 500 cc white polyethylene bottles. These bottles are thick walled, and pursuant to increasing environmental regulations must be cleaned and recycled rather than disposed. This necessitates that a large supply of bottles be carried in some type of a case or carton, with the empty bottles being replaced in the carton and returned to a central dispatch or supplier. This can be very inconvenient for police or other law enforcement officers who can carry only a limited amount of equipment or supplies, and those involved with testing large numbers of people as part of an federal, state, or private employee substance abuse testing programs In cold climates, water-based simulator solution can freeze despite the ethanol content, and the expansion upon freezing can crack or destroy the bottles In many instances this will only produce an inconvenient clean-up problem and possibly damage other equipment, but if undetected can cause a degradation or contamination of the simulator solution that will adversely affect the validity of the calibration.

Moreover, one potential source of error may be found in the manner in which the simulator solution is used. Since the simulator solution which is placed in the bottles must be analyzed and certified for accuracy, the bottles must also be sealed with a tamper-resistant or tamper-evidencing closure, or it is possible that the simulator solution may be contaminated or corrupted prior to use in calibrating the breath testing equipment. Once opened, the simulator solution may be spilled (affecting the total volume of fluid placed in the simulator) or allowed to evaporate (affecting the alcohol concentration of the simulator solution.) There is also the possibility that simulator solution will be replaced into the bottles and reused in order to lower operating costs, which would of course degrade the accuracy of any calibration, or that less than the full volume of simulator solution would be used for each calibration if the bottles can be resealed.

Some agencies prepare simulator solution by diluting a precisely measured aliquot of a concentrated simulator solution with water or a suitable inert fluid. However, this process can introduce significant errors as the result of improper procedures used in measuring the fluid or mixing the concentrate with the fluid. Moreover, any degradation or corruption of the concentrate may be amplified when the concentrate is diluted

BRIEF SUMMARY OF THE INVENTION

It is therefore one object of this invention to design a container for a breath alcohol simulator solution which requires a minimum of space and permits easy dispensing of the simulator solution without loss.

It is a related object of this invention to design the above container such that it may be used with simulator solutions which have been prepared and certified to have a set concentration, or alternately with a premeasured aliquot of concentrated solution that is diluted in water or an inert fluid.

It is another object of this invention to design the above container such that it may not practically be opened prior to use, and such that it evidences tampering and contamination or corruption of the simulator solution upon opening.

It is a related object of this invention to design the above container such that it may be easily disposed after use, and cannot be reused or resealed.

It is a further object of this invention to design the above container such that it will not be subject to damage if the simulator solution is frozen.

It is yet another object of this invention to design the above container such that it may be packaged in a front and top opening carton for easy access and verification of the number of containers remaining, particularly without removing the carton from a storage compartment or refrigerator.

It is a distinct object of this invention to design the above container such that it may be utilized in a specially designed breath alcohol simulator in which the fluid contents of the container are not removed from the container, but rather wherein the unopened container and fluid contents are placed within the breath alcohol simulator for calibration.

Briefly described, the breath alcohol simulator solution container of this invention comprises a self-standing 4 mil polyethylene bag having a removable label designating the quantity and calibration concentration of the fluid contained within the bag. The label may be removed from the bag and affixed to the breath alcohol simulator. A plurality of the filled bags are packaged in an upstanding position within a front and top opening carton having a pivoting lid for transportation, storage, and use. The bag may be torn open and the fluid contents poured into a cavity within the breath alcohol simulator, or the bag may be opened and placed partially or entirely within the breath alcohol simulator with an aerator extending into the bag beneath the fluid level. Alternately, the bag may be placed within a breath alcohol simulator having an aerator or aspirator equipped to puncture the bag, with the simulator solution then being discharged into the cavity, or the air passed through the simulator solution within the bag. In such a case, a mechanism for agitating the simulator solution within the bag may be placed within the bag prior to sealing, or may be disposed on the portion of the aerator or aspirator which punctures and enters the bag.

BRIEF DESCRIPTION OF THE DRAWINGS

FIG. 5 is a diagrammatic perspective view showing the breath alcohol simulator solution being dispensed from the breath alcohol simulator solution container of FIG. 1 through the open top of a breath alcohol simulator;

FIG. 6 is a diagrammatic perspective view showing the aerator and aspirator of a breath alcohol simulator being lowered through the open top of a breath alcohol simulator solution container of FIG. 1 disposed within a breath alcohol simulator;

FIG. 7 is a side sectional view of the breath alcohol simulator of FIG. 6 taken through line 7—7 of FIG. 6 with the cover seated on the cavity and the aerator and aspirator fully disposed within the breath alcohol simulator solution container of FIG. 1; and FIG. 8 is a side sectional view of an alternate embodiment of a breath alcohol simulator with an aerator puncturing the bottom and disposed within the breath alcohol simulator solution container of FIG. 1.

DESCRIPTION OF THE PREFERRED EMBODIMENTS

The breath alcohol simulator solution container of this invention is shown in FIGS. 1-8 and referenced generally therein by the numeral 10.

Figure 1:
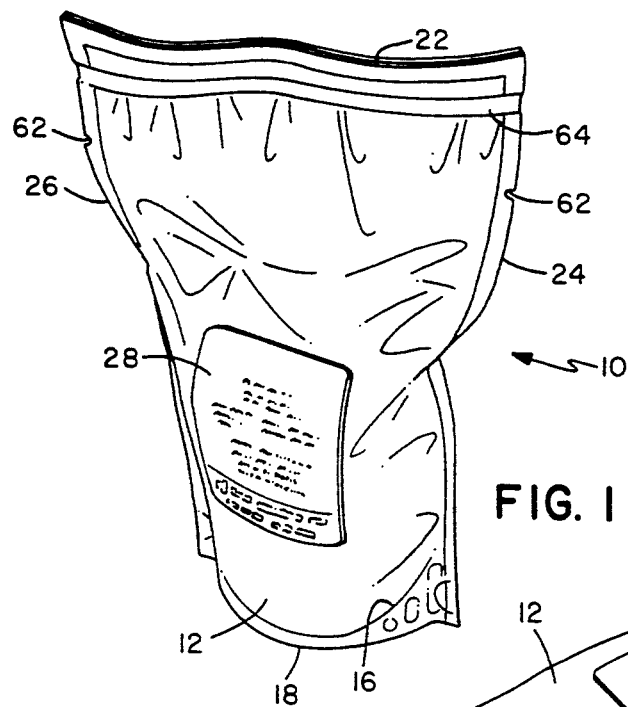
FIG. 1 is a perspective view of one embodiment of the breath alcohol simulator solution container of this invention in the upstanding position.
Figure 4:
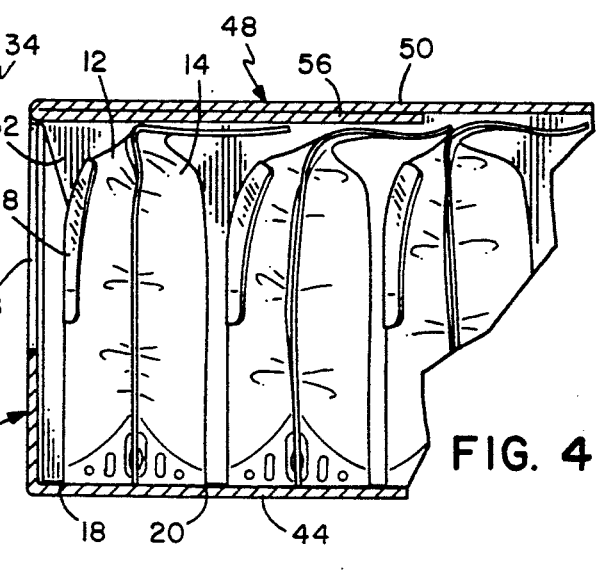
FIG. 4 is a partial side elevation view of the front and top opening carton and plurality of the breath alcohol simulator solution containers of FIG. 3 taken through line 4—4 in FIG. 3, with the front flap folded inwardly and upwardly.

Referring particularly to FIGS. 1 and 4, the container 10 comprises a transparent bag having a generally rectangular front wall 12, a generally rectangular rear wall 14, and a generally elliptical intermediate bottom wall 16 extending between and connected to both the front wall 12 and rear wall 14. The front wall 12, rear wall 14, and bottom wall 16 define a generally triangular pyramidal three-dimensional interior enclosure having a curved or arcuate bottom. The top edge and a substantial portion of the side edges of the front wall 12 are attached to the corresponding top edge and side edges of the rear wall 14, with the curved edges of the intermediate bottom wall 16 being attached to the front wall 12 and rear wall 14 and causing the front wall 12 and rear wall 14 to curve outward convexly away from a generally planar configuration when filled with liquid.

Due to the curvature of the front wall 12 and rear wall 14 caused by the generally elliptical bottom wall 16, the bottom edges 18, 20 of the front wall 12 and rear wall 14 will be spaced part and rest upon a generally planar surface, the bottom edges 18, 20 contacting that surface along a path such as an ellipse similar to the shape of the bottom wall 16. As such, when fluid is placed within the container 10 and the front wall 12 and rear wall 14 are bowed or pushed outwardly to their convex configuration, the container 10 will be self-supporting or free-standing in an upright position as shown particularly in FIGS. 1 and 4.

The front wall 12, rear wall 14, and bottom wall 16 are each fabricated from two coextruded plies or layers, the inner ply or barrier layer being a 0.1–0.5 mil polyethylene, with the outer ply or structural layer being 0.5–5.0 mil Nylon. Increasing the thickness of the higher modulus outer ply increases the strength and stability of the container 10 when it is oriented in the upright free-standing position The top edge 22 and side edges 24, 26 of the front wall 12 and rear wall 14, as well as the bottom wall 16, are joined together using a thermal or sonic welding process that produces an approximately 0.25 inch welded or bonded seal so that the container is impermeable and leak-proof to fluids including liquids and gases, and will not permit fluids or vapors to dissipate through the container 10 over a time equal to the normal shelf life of the simulator solution. The top edges 22 of the front wall 12 and rear wall 14 are sealed together using a conventional heat sealing process once the simulator solution has been dispensed into the container 10 through the open top.

In the preferred embodiment of the container 10, the combined thickness of the inner and outer plies is approximately 4.5 mils, but should not exceed 5 mils. The container 10 should be of a size sufficient to contain at least 500 cc of fluid and remain stable in the upright freestanding position, with a sufficient head space above the level of the fluid in the standing container 10 to permit the fluid to expand without breaking the container 10 if the fluid becomes fully frozen. A container 10 having a height of 9"and a width of 5" with an outside diameter of 1⅞"when filled has proven a suitable size for containing a 500 cc fluid volume.

Further details regarding the construction of a bag or container 10 of this type may be drawn from U.S. Pat. Nos. 4,837,849 to Erickson; 4,353,497 to Bustin, 3,380,646 to Doyen; 3,980,225 to Kan; and 3,437,258 to Kugler, the disclosures of which are incorporated herein by reference. In particular, the Erickson '849 patent discloses a bag or container 10 which provides a representative example for use in the breath alcohol simulator solution container 10.

A removable label 28 designating such items as the quantity and selected calibration concentration of the simulator solution container therein is affixed or adhered to the front wall 12 of the container 10, and may be peeled from the front wall 12 and selectively applied to an outer surface 30 of the breath alcohol simulator 32. The label 32 has a ink retentive surface which may be permanently marked with information concerning the performance of the calibration tests for which that simulator solution is used, and the label may be removed from the breath alcohol simulator 32 and selectively re-adhered to the container 10 or retained for evidentiary or record keeping purposes by adhering the label 28 to a written record.

Figure 2:
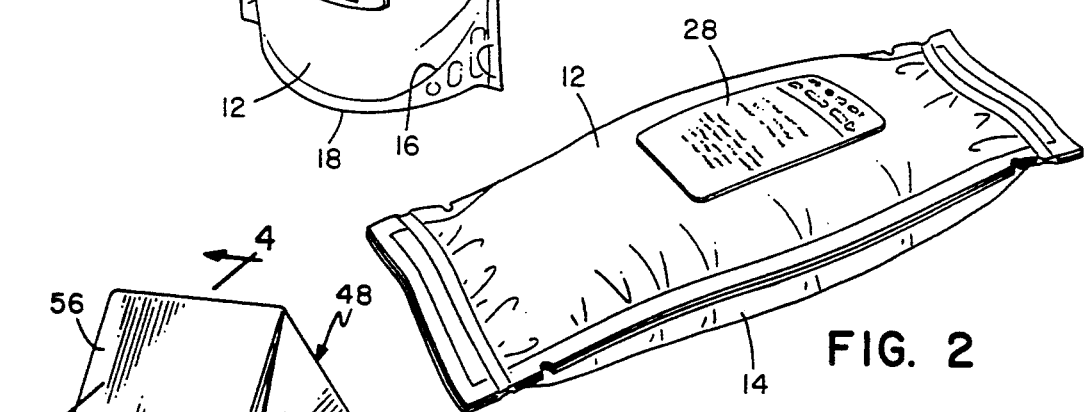
FIG. 2 is a perspective view of one embodiment of the breath alcohol simulator solution container of this invention in the flat horizontal position.

Alternately, a non-free-standing bag may be utilized for the container 10, particularly in uses of the container 10 within a specialized breath alcohol simulator 32 as described further below. As shown in FIG. 2, the freestanding container 10 or bag is also capable of being laid flat, the bottom wall 16 folding upwardly when no under vertical pressure to permit both ends of the container 10 to flatten so the container 10 will not roll and the front wall 12 and label 28 will remain facing upward.

The fluid contents of the breath alcohol simulator solution container 10 may comprise any conventional simulator solution for use in a breath alcohol simulator 32, either in the predetermined concentration as used within the breath alcohol simulator 32 or in a concentrated form which is diluted with water or an inert fluid. Because no generic term exists, the term alcohol is used herein to mean both ethanol or other organic alcohols, as well as natural, organic, or synthetic compounds of any type which react or function in substantially the same manner in a breath alcohol simulator and are suitable for use in calibrating a breath tester.

Figure 3:
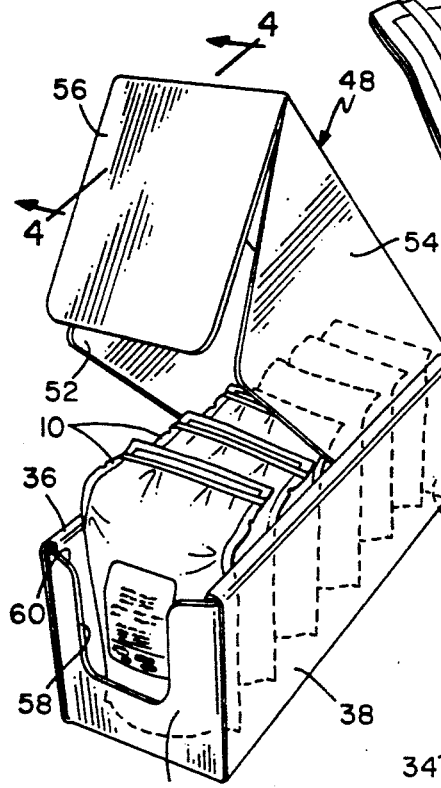
FIG. 3 is a front perspective view of the front and top opening carton containing a plurality of the breath alcohol simulator solution containers of FIG. 1 in the upstanding position.

Referring particularly to FIGS. 3 and 4, a plurality of the filled containers 10 are packaged in the upright freestanding position within a generally rectangular front and top opening carton 34. The carton 34 has a pair of opposing side panels 36, 38, a front panel 40, a rear panel 42, and a bottom panel 44 which are formed from a generally planar blank of double-faced corrugated cardboard or plastic sheet material that is scored and folded to the upright configuration and secured in a conventional manner. The side panels 36, 38, front panel 40, rear panel 42, and bottom panel 44 define a generally rectangular receptacle region having a width slightly greater than the width of one container 10, a depth sufficient such that six containers 10 may be placed in a single-file column or line within the receptacle region, and a height sufficient that each of the containers 10 may be received within the receptacle region in the upright freestanding position with the fluid level being disposed beneath the top edges 46 of the side panels 36, 38 and the head space of the containers 10 folded rearwardly and downwardly to be generally parallel with the top edges 46 of the side panels 36, 38.

Hingedly connected to the top edge of the rear panel 42 and formed integrally with the blank is a pivoting lid 48, the pivoting lid having a generally rectangular lid panel 50 sized to substantially cover the receptacle region, a pair of side flaps 52, 54 hingedly connected to and depending from the side edges of the lid panel 50 and each having a length approximately equal to the depth of the carton 34 and capable of being folded downwardly and received between the front panel 40 and rear panel 42, and a front flap 56 depending from the front edge of the lid panel 50 having a height and width approximately equal to the height and width of the carton 34 and capable of being folded downwardly and received between the side panels 36, 38.

Referring to FIG. 3, it may be seen that the front panel 40 of the carton 34 defines a large front opening 58 which extends downwardly from the top edge 60 of the front panel 40 a substantial portion of the height of the front panel 40 to permit viewing access to the frontmost or forwardmost container 10 received within the receptacle region. Referring to FIG. 4, it may be seen that once the cartons 34 has been initially opened, the front flap 56 of the pivoting lid 48 may be pivoted rearwardly and upwardly into parallel abutting contact with the inner surface of the lid panel 50, thereby allowing a user to visually inspect whether containers 10 remain in the front and top opening carton 34 without having to remove the carton 34 from a shelf, counter top, storage container, or refrigerator and open the pivoting lid 48.

The front opening 58 is sized such that the forwardmost container 10 may be selectively removed by a user, which may require manual reorientation or deformation of the forwardmost container 10 by the user, but such that the forwardmost container 10 cannot accidentally pass through the front opening 58 when the forwardmost container 10 is in the upright position, such as when the carton 34 is tilted forward.

In use, the pivoting lid 48 is moved from the closed position in covering relation to the carton 34 to an open position as shown in FIG. 3, and a container 10 of simulator solution is removed from the receptacle region of the carton 34 by the user.

The user then tears open the top or a top corner of the container 10 using one of a pair of nicks 62 formed in the opposing side edges of the container 10 at a position above the fluid level and beneath the line formed by the conventional heat sealing closure 64.

Once the container 10 has been opened, the fluid contents of the container may be poured into a cavity or chamber 66 within the breath alcohol simulator 32 as shown diagrammatically in FIG. 5. The head or cover 68 of the breath alcohol simulator 32 may then be placed over the chamber 66 and the breath alcohol simulator 32 may be operated. The cover 68 or other component of the breath alcohol simulator 32 includes an air inlet 70 or aerator that is eventually disposed beneath the fluid level within the chamber 66, and an air outlet 72 or aspirator disposed at or above the fluid level within the chamber 66. The cover 68 conventionally includes a motor driven stirrer which depends beneath the fluid level within the chamber 66 and assures constant and uniform circulation of the fluid when the simulator 32 is operated. The air inlet 70 or aerator bubbles air or an inert gas through the simulator solution allowing the air or gas to become saturated with a predetermined content of alcohol vapor, and the air outlet 72 withdraws that air so that it may be delivered to a breath tester (not shown) for calibration.

Alternately, the entire top of the container 10 may be opened and removed, and the container 10 may be placed either partially or entirely within the chamber 66 of the breath alcohol simulator 32 with the air inlet 70 or aerator extending into the container 10 through the open top thereof and beneath the fluid level as shown particularly in FIGS. 6 and 7. In this case, it may be preferable to fold the top edges 22 of the front wall 12 and rear wall 14 of the container 10 downwardly over the side 30 of the breath alcohol simulator 32 such that the cover 68 will secure the top edges 22 and maintain the container 10 in an upright position.

Again alternately, the aerator or air inlet 70 or the aspirator or air outlet 72 or both may be equipped with a sharpened distal tip 74 which will puncture the container 10 when the container 10 is initially placed within the chamber 66, or when the cover 68 is secured onto the breath alcohol simulator 32, as shown in FIG. 8. The simulator solution may then be discharged into the chamber 66, or the air may be passed directly through the simulator solution while it remains substantially within the container 10, thereby allowing more convenient disposal and cleaning when the calibration is complete and the simulator solution must be replaced.

In using an aerator or air inlet 70 or aspirator or air outlet 72 equipped with a sharpened distal tip 74, one alternative is to omit the chamber 66 of the breath alcohol simulator 32, and use a container 10 such as shown in FIGS. 1 or 2 in a manner similar to an intravenous apparatus, but which may also be a bottle or a distinct form of a puncturable container such as a polyethylene lined fiberboard box. In such a case, a separate magnetic stirring mechanism may be disposed adjacent to the container 10 if necessary, with a magnetic stirring bar 76 initially disposed within the container 10. The container 10 should have sufficient head space to permit the aerator or air inlet 70 to be disposed beneath the fluid level while the aspirator or air outlet 72 remains above the fluid level but within the head space of the container 10, with the puncture or partial opening in the container 10 being substantially sealed around the aerator or air inlet 70 and aspirator or air outlet 72 to ensure that air does not escape from the container 10 except through the aspirator or air outlet 72.

In the alternate examples for use of the container 10 described above with relation to FIGS. 7 and 8, it may be necessary to initially place a magnetic stirring bar 76 within the container 10 prior to sealing the container 10 which may be coupled to a magnetic drive incorporated into the breath alcohol simulator 32, or to equip the air inlet 70 or air outlet 72 with a rotating stirring mechanism or agitator to adequately mix the simulator solution during calibration.

While the preferred embodiments of the above breath alcohol simulator solution container 10 and the front and top opening carton 34 have been described in detail above with reference to the attached drawing Figures, along with the method of using same, it is understood that various changes and adaptations may be made in either the breath alcohol simulator solution container 10 and the front and top opening carton 34 without departing from the spirit and scope of the appended claims.

What is claimed is:

1. A breath alcohol simulator solution container and simulator solution assembly, said breath alcohol simulator solution container and simulator solution assembly comprising:
    a bag, said bag constructed from a plastic sheet material, said bag having a front wall, a rear wall, and a bottom wall, said bag being substantially freestanding and self-supporting when said bag is selectively placed in an upright position; and
    a predetermined volume of a simulator solution having a fixed alcohol content and being initially contained within said bag, said bag being sealed so as to resist and evidence either tampering with said bag or corruption of said predetermined volume of said simulator solution.

2. The breath alcohol simulator solution container and simulator solution assembly of claim 1 wherein the plastic sheet material has a thickness of no more than approximately five mils.

3. The breath alcohol simulator solution container and simulator solution assembly of claim 1 for use with a breath alcohol simulator and a written record, said assembly further comprising:
    a label, said label being removably adhered to the bag such that said label may be removed and selectively adhered to the breath alcohol simulator and selectively re-adhered to the bag or adhered to the written record for evidentiary purposes.

4. The breath alcohol simulator solution container and simulator solution assembly of claim 3 wherein the label has an ink retentive surface which may be selectively and permanently marked with record keeping information.

5. The breath alcohol simulator solution container and simulator solution assembly of claim 1 wherein the predetermined volume of the simulator solution is filled in the bag to a fluid level, the bag further including a head space disposed above said fluid level sufficient to permit the predetermined volume of the simulator solution to freeze without damaging the bag.

6. The breath alcohol simulator solution container and simulator solution assembly of claim 1 wherein the alcohol content of the predetermined volume of the simulator solution is such that the simulator solution has a predetermined concentration, said predetermined concentration being approximately equal to a desired concentration at which the simulator solution is used within a breath alcohol simulator.

7. A breath alcohol simulator solution, container and carton assembly comprising:
  a plurality of bags, each of said plurality of bags constructed from a plastic sheet material, each of said plurality of bags having a front wall and a rear wall and a bottom wall, each of said plurality of bags being substantially free-standing and self-supporting when selectively placed in an upright position;
  a plurality of predetermined volumes of a simulator solution having a fixed alcohol content, each of said plurality of volumes of said simulator solution being initially contained within an individual one of said plurality of bags, each of said plurality of bags being sealed so as to resist and evidence either tempering with said plurality of bags or corruption of said predetermined volumes of said simulator solution; and
  a carton having a receptacle region, said receptacle region of said carton having a depth and a width sufficient to receive said plurality of bags therein, said plurality of bags being disposed within said receptacle region in a single-file column.

8. The breath alcohol simulator solution, container, and carton assembly of claim 7 wherein the plastic sheet material has a thickness of no more than approximately five mils.

9. The breath alcohol simulator solution container, and carton assembly of claim 7 wherein the carton has a generally open top, the assembly further comprising:
  a lid, said lid being hingedly connected to the carton and movable between a closed position in covering relation to the open top and an open position displaced from said closed position.

10. The breath alcohol simulator solution, container, and carton assembly of claim 9 wherein the carton has a front panel and a rear panel and a pair of opposing side panels, and wherein the lid includes a lid panel hingedly connected to the rear panel which may be selectively pivoted between the closed position and the open position.

11. The breath alcohol simulator solution container, and carton assembly of claim 10 wherein the front panel of the carton defines a front opening and the lid panel has a front edge, and wherein the lid further includes a front flap hingedly connected to and depending from said front edge of the lid panel, said front flap being selectively received within the receptacle region of the carton in bloc)king relation to said front opening when the lid panel is pivoted to the closed position.

12. The breath alcohol simulator solution, container, and carton assembly of claim 11 wherein the front flap may be selectively pivoted rearwardly and upwardly and into parallel abutting contact with the lid panel when the lid panel is pivoted to the closed position, whereby a user may visually inspect whether a number of the plurality of bags remain in the receptacle region of the carton without pivoting the lid panel to the open position.

13. The breath alcohol simulator solution, container, and carton assembly of claim 11 wherein the front opening has a height and a width, said height and said width being such that a frontmost bag of the plurality of bags within the receptacle region cannot pass through the front opening when said frontmost bag is in the upright position.

14. The breath alcohol simulator solution, container, and carton assembly of claim 11 wherein the front opening has a height and a width, said height and said width being such that a frontmost bag of the plurality of bags within the receptacle region cannot accidentally pass through the front opening when said frontmost bag is in the upright position, but where a user may intentionally remove said frontmost bag through the front opening.

15. The breath alcohol simulator solution container and simulator solution assembly of claim 10 wherein the plurality of predetermined volumes of the simulator solution are filled into the plurality of bags such that the plurality of predetermined volumes of the simulator solution rise to a fluid level within each of the plurality of bags, each of the plurality of bags further including a head space disposed above said fluid level sufficient to permit the plurality of predetermined volumes of the simulator solution to freeze without damaging the plurality of bags.

16. The breath alcohol simulator solution container and simulator solution assembly of claim 10 wherein the opposing side panels of the carton each have a height, said height being generally equal to or slightly greater than the fluid level within each of the plurality of bags, and wherein the head space of each of the plurality of bags is folded rearwardly so as to be generally parallel with the lid panel.

* * * * *